US008299433B2

(12) United States Patent
Majewski et al.

(10) Patent No.: US 8,299,433 B2
(45) Date of Patent: Oct. 30, 2012

(54) MULTI-CHANNEL OPTICAL CELL

(75) Inventors: Alexander Majewski, Fairfield, CT (US); Robert Noll, Fairfield, CT (US); Malcolm J. MacFarlane, Brookfield, CT (US)

(73) Assignee: Goodrich Corporation, Charlotte, NC (US)

( * ) Notice: Subject to any disclaimer, the term of this patent is extended or adjusted under 35 U.S.C. 154(b) by 258 days.

(21) Appl. No.: 12/731,909

(22) Filed: Mar. 25, 2010

(65) Prior Publication Data

US 2011/0233406 A1    Sep. 29, 2011

(51) Int. Cl.
*G01J 5/00* (2006.01)
*G01J 1/00* (2006.01)
*G02B 17/00* (2006.01)

(52) U.S. Cl. .................. 250/338.1; 250/336.1; 359/365
(58) Field of Classification Search ............ 250/336.1, 250/338.1; 356/51, 244, 246, 440; 359/362, 359/365
See application file for complete search history.

(56) References Cited

U.S. PATENT DOCUMENTS

| | | | |
|---|---|---|---|
| 2,779,230 A | 1/1957 | White | |
| 3,726,598 A * | 4/1973 | Gilby et al. | 356/244 |
| 4,626,078 A | 12/1986 | Chernin et al. | |
| 5,267,019 A | 11/1993 | Whittaker et al. | |
| 5,798,880 A * | 8/1998 | Yamamoto | 359/857 |
| 5,818,578 A | 10/1998 | Inman et al. | |
| 5,883,518 A | 3/1999 | Borden | |
| 5,903,358 A | 5/1999 | Zare et al. | |
| 5,966,019 A | 10/1999 | Borden | |
| 6,348,683 B1 | 2/2002 | Verghese et al. | |
| 6,466,322 B1 | 10/2002 | Paldus et al. | |
| 6,486,474 B1 | 11/2002 | Owen et al. | |
| 6,500,618 B1 | 12/2002 | Woolard et al. | |
| 6,865,198 B2 | 3/2005 | Taubman | |
| 7,174,037 B2 | 2/2007 | Arnone et al. | |
| 7,271,594 B2 | 9/2007 | Abreu et al. | |
| 7,291,839 B1 | 11/2007 | Demers et al. | |

(Continued)

FOREIGN PATENT DOCUMENTS

GB    2 391 310 A    2/2004

(Continued)

OTHER PUBLICATIONS

White, J. U. *Long Optical Paths of Large Aperture*, Journal of the Optical Society of America, vol. 32, No. 5, May 1942, pp. 285-288.

(Continued)

*Primary Examiner* — David Porta
*Assistant Examiner* — Faye Boosalis
(74) *Attorney, Agent, or Firm* — Andrew T. Spence

(57) ABSTRACT

An apparatus is provided that includes a field reflector and a plurality of pairs of object reflectors. The apparatus also includes a plurality of source and detector port pairs, where each source port is configured to pass a beam of radiation, and each detector port is configured to receive a beam of radiation. The source and detector ports of each pair are positioned proximate an outer edge of the field reflector such that an optical axis of the field reflector lies between the respective source port and detector port. The object reflectors and source and detector port pairs are arranged such that each source and detector port pair is associated with a respective pair of object reflectors forming a distinct channel, where the source and detector port pair, and centers of the associated pair of object reflectors, of each channel lie in a distinct plane.

27 Claims, 4 Drawing Sheets

U.S. PATENT DOCUMENTS

| | | |
|---|---|---|
| 7,352,463 B2 | 4/2008 | Bounaix |
| 2002/0067480 A1 | 6/2002 | Takahashi |
| 2004/0114939 A1 | 6/2004 | Taylor |

FOREIGN PATENT DOCUMENTS

| | | |
|---|---|---|
| WO | WO 03/005510 A1 | 1/2003 |
| WO | WO 2004/083796 A1 | 9/2004 |

OTHER PUBLICATIONS

Hindle, F. et al., *Long Path Length cw-THz Spectrometer Using a Multipass Cell*, Infrared, Millimeter and Terahertz Waves, 2008. IRMMW-THZ 2008. 33rd International Conference on, IEEE, Piscataway, NJ, Sep. 2008, 2 pages.

European Search Report for Application No. EP 11 25 0314 dated Jul. 26, 2011.

Armerding, W. et al., *Multipass Optical Absorption Spectroscopy: a Fast-Scanning Laser Spectrometer for the in situ Determination of Atmospheric Trace-Gas Components, in Particular OH*, Applied Optics, vol. 35, No. 21, (1996), pp. 4206-4219.

Auton, J. P., *Infrared Transmission Polarizers by Photolithography*, Applied Optics, vol. 6, No. 6, (1967), pp. 1023-1027.

Blickensderfer, R. P. et at., *A Long Path, Low Temperature Cell*, Applied Optics, vol. 7, No. 11, (1968), pp. 2214-2217.

Brown, E. R. et al., *Coherent Millimeter-Wave Generation by Heterodyne Conversion in Low-Temperature-Grown GaAs Photoconductors*, J. Appl. Phys., 73(3), (1993), pp.1480-1484.

Edwards, T. H., *Multiple-Traverse Absorption Cell Design*, Journal of the Optical Society of America, vol. 51, No. 1, (1961), pp. 98-102.

Engel, G. S. et al., *Precise Multipass Herriott Cell Design: Derivation of Controlling Design Equations*, Optics Letters, vol. 32, No. 5, (2007), pp. 704-706.

Engeln, R. et al., *Phase Shift Cavity Ring Down Absorption Spectroscopy*, Chemical Physics. Letters, 262, (1996), pp. 105-109.

Gregory, I. S. et al., *Resonant Dipole Antennas for Continuous-Wave Terahertz Photomixers*, [online] [retrieved May 24, 2010]. Retrieved from the Internet: <URL: http://adsabs.harvard.edu/abs/2004Ap-PhL..85.1622G>. 1 page.

Harmon, S. A. et al., *Part-Per-Million Gas Detection From Long-Baseline THz Spectroscopy*, Applied Physics Letters, vol. 85, No. 11, (2004), pp. 2128-2130.

Hayden, A. et al., *Determination of Trace-Gas Amounts in Plumes by the Use of Orthogonal Digital Filtering of Thermal-Emission Spectra*, Applied Optics, vol. 35, No. 16, (1996), pp. 2802-2809.

Herbelin, J. M. et al., *Sensitive Measurement of Photon Lifetime and True Reflectances in an Optical Cavity by a Phase-Shift Method*, Applied Optics, vol. 19, No. 1, (1980), pp. 144-147.

Lehmann, K. K. et al., *The Superposition Principle and Cavity Ring-Down.Spectroscopy*; J. Chem. Phys., vol. 105, No. 23, (1996), pp. 10263-10277.

McCubbin, Jr., T. K. et al., *A White-Type Multiple-Pass Absorption Cell of Simple Construction*, Applied Optics, vol. 2, No. 7, (1963), pp. 764-765.

Mouret, G. et al., *THz Media Characterization by Means of Coherent Homodyne Detection, Results and Potential Applications*, Appl. Phys., B89, (2007), pp. 395-399.

Pickett, H. M. et al., *A New White Type Multiple Pass Absorption Cell*, Applied Optics, vol. 9, No. 10, (1970) pp. 2397-2398.

Rayl, G. J., *Multiple Traversal Absorption Cell of Minimum Volume: Design*, Applied Optics, vol. 15, No. 4, (1976), pp. 921-928.

Robert, C., *Simple, Stable, and Compact Multiple-Reflection Optical Cell for Very Long Optical Paths*, Applied Optics, vol. 46, No. 22, (2007), pp. 5408-5418.

Scherer, J. J. et al., *Cavity Ringdown Laser Absorption Spectroscopy: History, Development, and Application to Pulsed Molecular Beams*, Chem. Rev., 97, (1997),pp, 25-51.

Siegman, *11.5 Optical-Cavity Mode Frequencies*, Chapter 11: Laser Mirrors and Regenerative Feedback, pp. 435-437 (undated).

Ulrich, P. et al., *Variable Metal Mesh Coupler for Far Infrared Lasers*, Applied Optics, vol. 9, No. 11, (1970), pp. 2511-2516.

Verghese, S. et al., *Highly Tunable Fiber-Coupled Photomixers with Coherent Terahertz Output Power*, IEEE Transactions on Microwave Theory and Techniques, vol. 45, No. 8,(1997) pp. 1301-1309.

Verghese, S. et al., *Generation and Detection of Coherent Terahertz Waves Using Two Photomixers*, Applied Physics Letters, vol. 73, No. 26, (1998), pp. 3824-3826.

Verghese, S. et al., *The Photomixer Transceiver*, Invited Paper, SPIE Conference on Terahertz Spectroscopy and Applications, San Jose, CA, Jan. 1999, pp. 7-13.

White, J. U., *Very Long Optical Paths in Air*, J. Opt. Soc. Am., vol. 66, No. 5, (1976), pp. 411-416.

Zalicki, P. et al., *Cavity Ring-Down Spectroscopy for Quantitative Absorption Measurements*, J. Chem. Phys., 102 (7), (1995), pp. 2708-2717.

U.S. Appl. No. 12/712,736, filed Feb. 25, 2010; In re: Majewski et al., entitled *System and Method for Magnitude and Phase Retrieval by Path Modulation*.

\* cited by examiner

MULTI-CHANNEL OPTICAL CELL

FIELD OF THE INVENTION

Exemplary embodiments of present invention generally relate to an optical cell through which electromagnetic signals propagate and, more particularly, a multi-channel optical cell through which electromagnetic signals with different frequencies may simultaneously propagate.

BACKGROUND OF THE INVENTION

Recently, the development of unique sources and detectors in the terahertz (THz) region explored the unique rotational spectral features of compound molecules for toxic gas discrimination and detection. The THz spectral region presents some unique challenges not usually faced in the visible or infrared (IR) regions. Multiple stray unwanted reflections or standing waves may be more severe at THz and the physical optics propagation of the radiation may present a unique challenge to the instrument designer of the light path in the instrument. In particular, THz radiation may not stay collimated over long distances because of its long wavelength. Plane waves may rapidly propagate and translate to spherical waves. Also, beam sizes tend to be larger than their cousins at shorter wavelengths.

For shorter wavelengths, the light source and light path in the so-called White cell are designed to provide multiple bounces between three spherical mirrors, reflectors or the like in its elementary form. One of the three mirrors is often referred to as a field mirror, and the other two mirrors are often referred to as object mirrors. A light source and a detector may be located at symmetric positions about the optical axis of the field mirror and near its surface. The source may be constructed to produce a spherical wave that may be sent to one of the object mirrors. The object mirrors, then, may refocus the beam to the field mirror. The small focused spot (sometimes referred to as an "image") at a point of reflection on the field mirror may be redirected to the second object mirror as a spherical wave which, in turn, may focus the light back to a new spot on the field mirror. The more spots on the spherical mirror the longer the light path through the cell and the more sensitivity may be provided to a spectrometer in measuring absorption of the gas in the cell. The design then walks the spots over the field mirror until the spot can be placed on the detector. For more information on the White cell, see John U. White, *Long Optical Paths of Large Aperture*, 32 J. OPT. SOC. AM. 285-288 (1942).

Because of the long wavelength of THz radiation, the spots on the field mirror may be much larger than visible or IR spots. Also, the beam propagation as a function of wavelength may cause severe shifts in focus over a wide band of THz wavelengths. These issues may cause aberrated spots and loss of throughput as the beam divergence may vary significantly with wavelength. The larger spots and packaging constraints may limit the number of light bounces (path length) such a cell can achieve compared to shorter wavelength spectrometers.

SUMMARY OF THE INVENTION

In light of the foregoing background, example embodiments of the present invention provide an improved multi-channel optical cell. According to one aspect of example embodiments of the present invention, an apparatus is provided that includes a field reflector and a plurality of pairs of object reflectors, each of which has an optical axis and a reflective surface, the reflective surfaces of the object mirrors being arranged to face the reflective surface of the field reflector. The apparatus also includes a plurality of source port and detector port pairs facing the reflective surfaces of the object reflectors, where each source port is configured to pass a beam of radiation to propagation between the field reflector and object reflectors, and each detector port is configured to receive a beam of focused radiation propagating between the field reflector and object reflectors. The source port and detector port of each pair is positioned proximate an outer edge of the field reflector such that the optical axis of the field reflector lies between (e.g., in a symmetric position between) the respective source port and detector port. Thus, a beam of radiation passed by or through the source port may propagate and reflect between the field reflector and respective pair of object reflectors until the beam reaches the respective detector port. However, the source port and detector port of each pair lie on a chord of the field reflector that is displaced from, but parallel to, the diameter of the field reflector, which may allow for multiple rows of spots on the field mirror and thereby provide a longer path length than a single row of spots.

The object reflectors and source port and detector port pairs of this aspect are arranged such that each source port and detector port pair is associated with a respective pair of object reflectors forming a distinct channel, where the source port and detector port pair, and the centers of the associated pair of object reflectors, of each channel lie in a distinct plane. The centers of the pair of object reflectors may lie on a line parallel to the diameter of the field mirror. And in such instances, when the respective source port and detector port lie on a chord of the field reflector as indicated above, the distinct plane in which the port pair and reflector pair lies may be tilted some what from the axis (optical axis) of the field reflector. In various instances, for each channel, the chord along which the source port and detector port lie may be displaced from the diameter of the field reflector.

The object reflectors and source port and detector port pairs may be arranged such that the distinct planes of the channels intersect with a non-obtuse angle of intersection of approximately 360°/2n, where n represents the number of channels. Thus, for two channels, the planes may intersect at approximately a right angle, and for three channels, the planes may intersect at approximately a 60° angle.

The object reflectors may also be arranged around a common point on the optical axis of the field reflector, where the common point may be equidistant between the object reflectors. The field and object reflectors may be spherical or aspherical, concave reflectors, and may be arranged in a quatrefoil shape or a circle around the common point. For each channel, the source port and detector port may lie on a chord of the field reflector, and the object reflectors may be tilted at an angle along an axis perpendicular to the respective chord and perpendicular to the optical axis of the field reflector.

Each source port may be configured to pass a beam of radiation in a distinct frequency band. The distinct frequency band for each channel may be in the terahertz spectral region. In other instances, including those in which the source ports include at least a first source port and a second source port, the first source port may be configured to pass a beam of radiation in the terahertz spectral region, and the second source port may be configured to pass a beam of radiation in the infrared or visible spectral region. And when the source ports further include a third source port, the second source port may be configured to pass a beam of radiation in the infrared spectral region, and the third source port may be configured to pass a beam of radiation in the visible spectral region.

According to another aspect of example embodiments of the present invention, an apparatus is provided that includes a field reflector, and first and second channels, and may also include a third channel. The first channel includes a first pair of object reflectors, and a first source port and a first detector port. The first source port and detector port may be positioned proximate an outer edge of the field reflector along a first chord of the field reflector that is displaced from, but parallel to, the diameter of the field reflector, and may be positioned such that the respective ports are equidistant from the field mirror axis (optical axis). The second channel includes a second pair of object reflectors, and a second source port and a second detector port. Similar to the first source and detector ports, the second source and detector ports may be positioned proximate the outer edge of the field reflector along a second chord of the field reflector that, similar to the first chord, is displaced from, but parallel to, the diameter of the field reflector. Also similar to the first source and detector ports, the second source and detector ports may also be positioned such that the respective ports are equidistant from the field mirror axis. And if included, the third channel includes a third pair of object reflectors, and a third source port and a third detector port that may be positioned similar to the first and second source and detector port pairs.

Relative to this aspect, each of the object reflectors has an optical axis, and has a reflective surface arranged to face a reflective surface of the field reflector. The first source port and first detector port, and the centers of the first pair of object reflectors, lie in a first plane. The second source port and second detector port, and the centers of the second pair of object reflectors, lie in a second plane that is distinct from the first plane. And if included, the third source port and third detector port, and the centers of the third pair of object reflectors, lie in a third plane that is distinct from both the first and second planes.

BRIEF DESCRIPTION OF THE DRAWINGS

Figure 1:
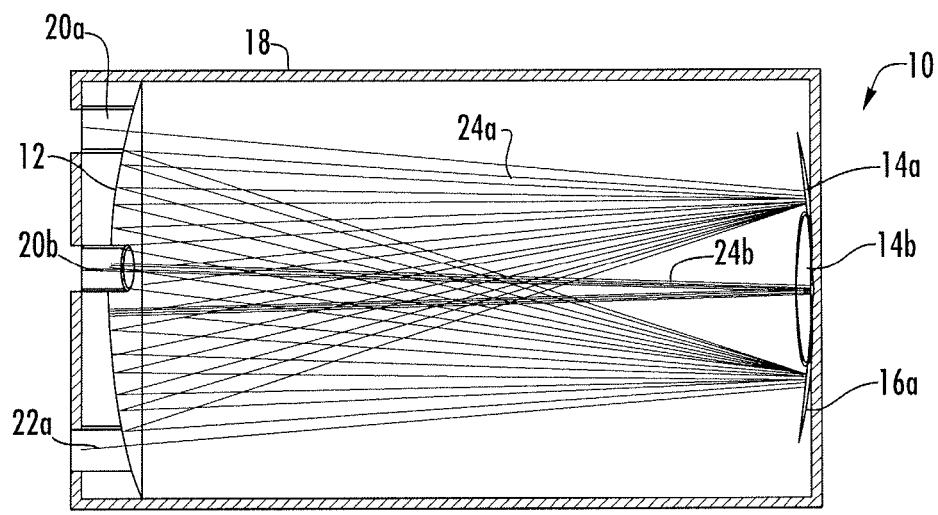
Figure 2:
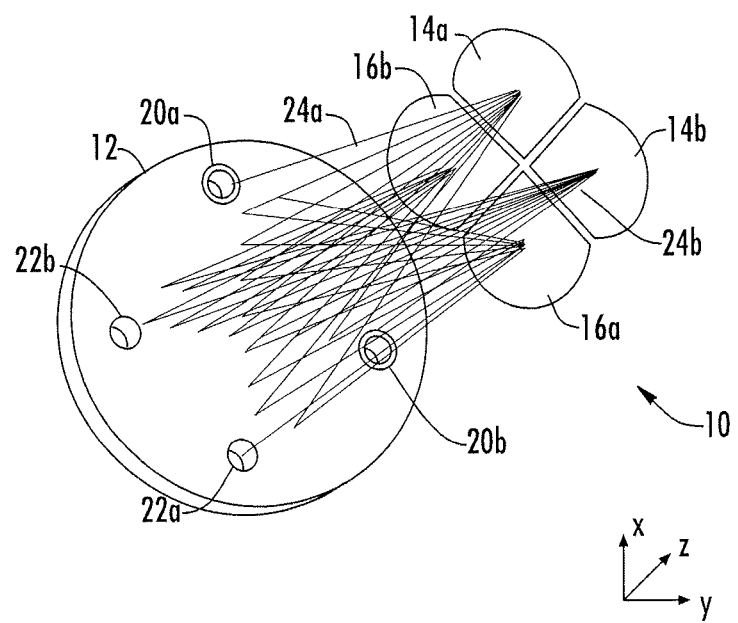
Figure 3:
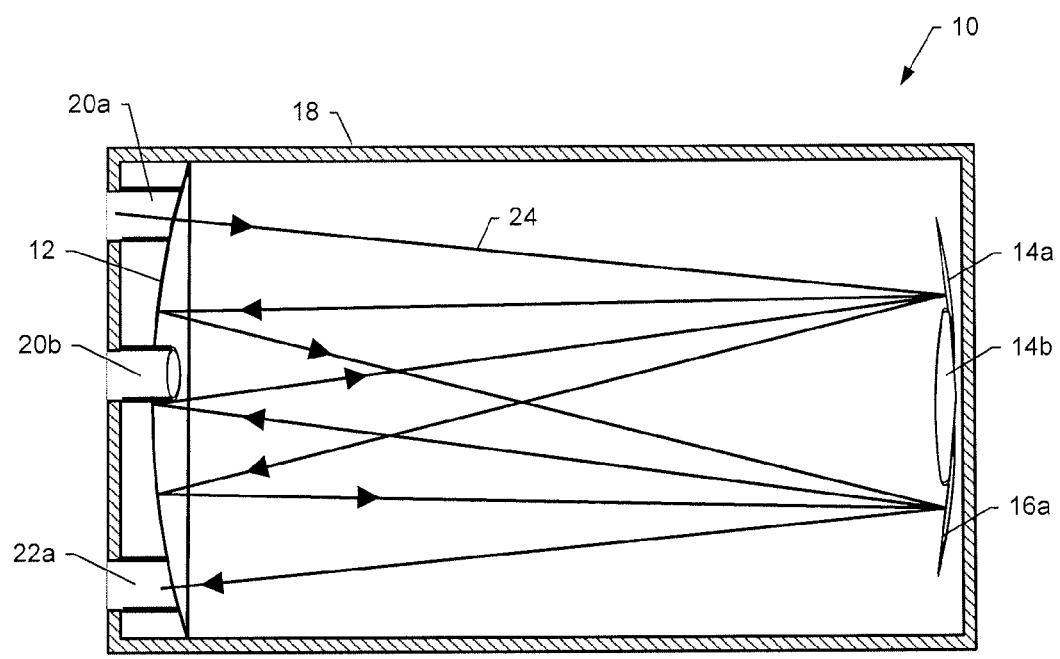
Figure 3:
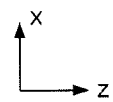
Figure 4:
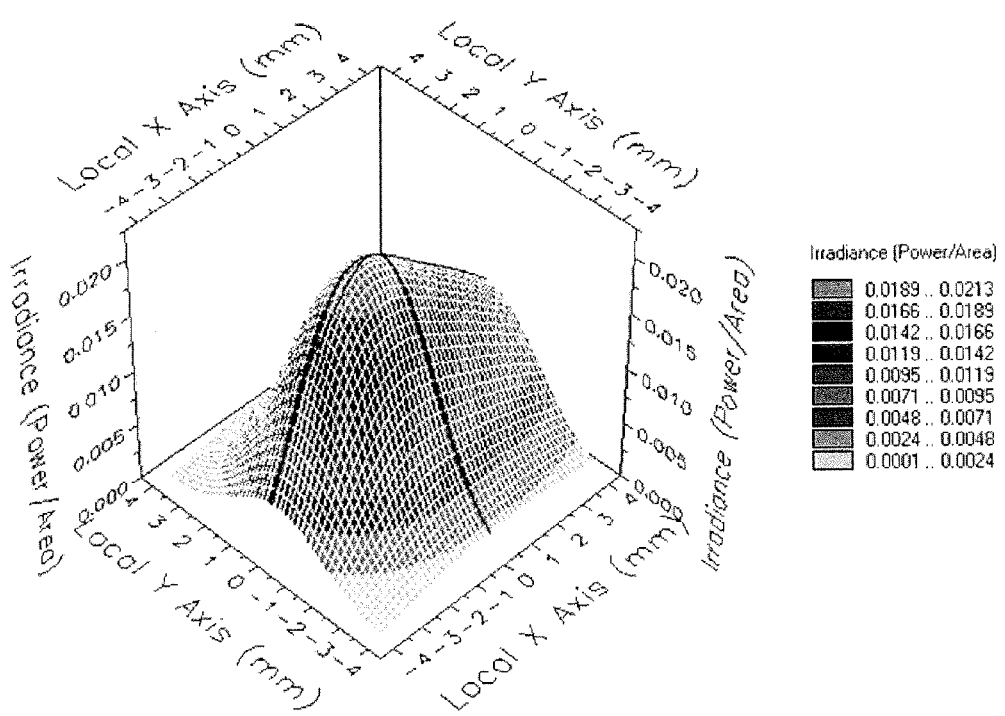
Figure 5:
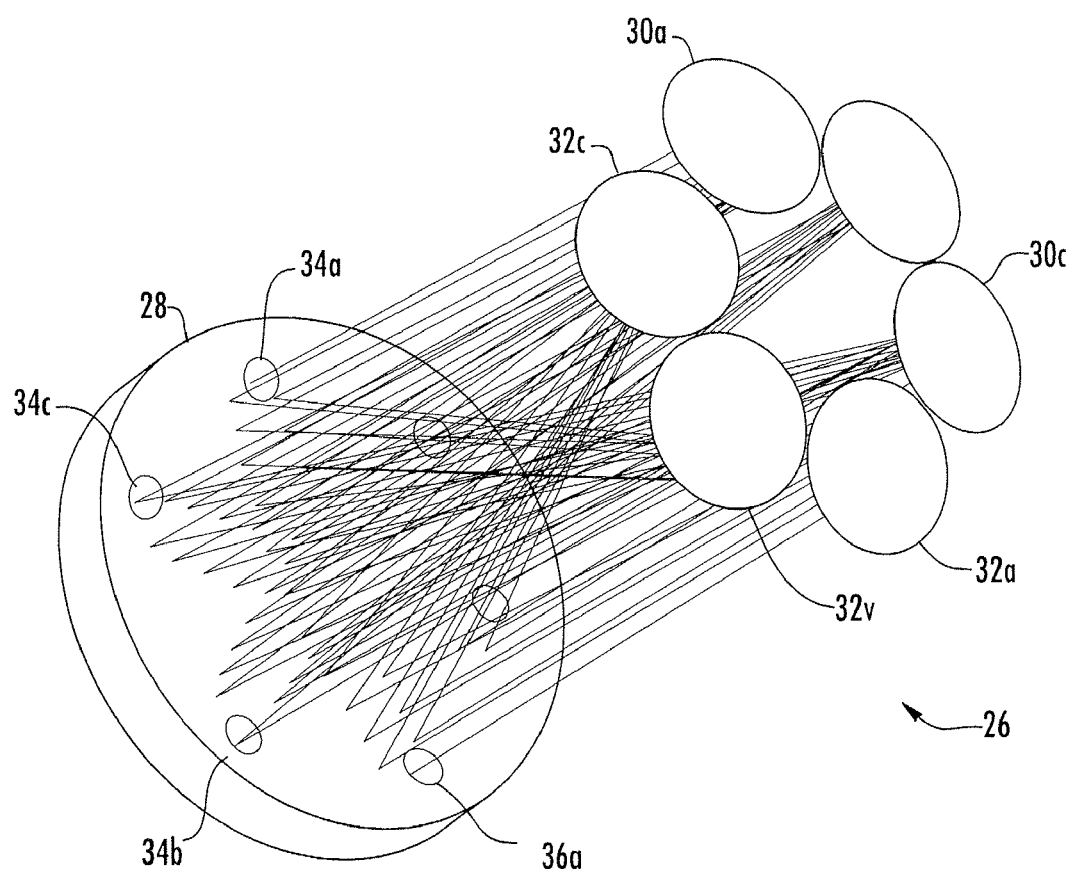

Having thus described the invention in general terms, reference will now be made to the accompanying drawings, which are not necessarily drawn to scale, and wherein:

FIGS. 1 and 2 illustrate side and perspective views dual-channel optical cell according to example embodiments of the present invention;

FIG. 3 illustrates the a side view of a dual-channel optical cell highlighting propagation of a beam through one of its channels, according to example embodiments of the present invention;

FIG. 4 is a graph illustrating an example of the irradiance (power per area) of a beam that may be measured by a detector of a multi-channel optical cell, according to example embodiments of the present invention; and FIG. 5 is a perspective view of a three-channel optical cell according to other example embodiments of the present invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In this regard, reference may be made herein to a number of mathematical or numerical expressions or values, and to a number of positions of various components, elements or the like. It should be understood, however, that these expressions, values, positions or the like may refer to absolute or approximate expressions, values or positions, such that exemplary embodiments of the present invention may account for variations that may occur in the multi-channel optical cell, such as those due to engineering tolerances. Like numbers refer to like elements throughout.

Example embodiments of the present invention are directed to a multi-channel optical cell that may allow increased sensitivity while retaining a wide spectral band, as compared to a conventional optical cell. As principally shown and described herein, the multi-channel optical cell is a dual-channel optical cell that includes two channels, each of which has a respective transmitter or source and receiver or detector. It should be understood, however, that the multi-channel optical cell may include three, four or more channels depending upon operating wavelength and path length requirements.

Moreover, the multi-channel optical cell of example embodiments of the present invention will be primarily described in conjunction with signals in the THz (or mmW) region of the electromagnetic spectrum. But the multi-channel optical cell of example embodiments of the present invention may be utilized in conjunction with a variety of other applications, both within and outside the THz region of the electromagnetic spectrum. More particularly in the context of a dual-channel optical cell, for example, one channel may be configured to operate in a highly-selective, slightly-narrow THz band, while the other channel may be configured to operate in a wider less sensitive band. Other example configurations include the following:

One infrared (IR) channel and one THz channel that, in the context of a spectrometer system, may a user with instrumentation to cover higher-frequency molecular vibration spectra as well as lower frequency rotational spectra simultaneously on the same gas;

One visible channel and one THz channel; and

One visible channel, one IR channel and one THz channel.

FIGS. 1 and 2 illustrate side and perspective views of a dual-channel optical cell 10 according to example embodiments of the present invention. As shown, the dual-channel optical cell may include a concave field reflector 12 and a pair of object reflectors 14, 16 for each channel (shown as object reflectors 14a, 16a for a first channel, and 14b, 16b for a second channel). The reflectors may comprise any of a number of different components capable of reflecting a beam of radiation (electromagnetic wave), such as mirrors, retroreflectors or the like, one or more of which may include a coating or other element to facilitate or otherwise aid such reflection. The object reflectors may be separate reflectors, or two or more of the object reflectors may be formed from a single reflector.

The field reflector 12 and object reflectors 14, 16 may be concave reflectors that have reflecting surfaces of any of a number of different shapes. In one example embodiment, the reflectors including the field and object reflectors, may be spherical or aspherical, concave reflectors. The object reflectors 14, 16 may be conceptually considered to be segments of a common parent, object reflector whose center is on the axis (optical axis) of the field reflector 12. As segments, the object reflectors may be positioned such that their centers are equidistant from the optical axis of the parent object reflector, and hence, the optical axis of the field reflector. The object reflectors for a common channel may have the same parent prescription (optical properties—e.g., radius of curvature, position and orientation relative to the field reflector), whereas object reflectors for different channels may have different parent prescriptions.

In one example embodiment, the field and object reflectors 12, 14, 16 may be spherical, concave reflectors, and the object reflectors may be positioned so their centers lie on a line parallel to the diameter of the field reflector but each tilted to produce a desired number of spots on the field reflector, and hence, a desired path length of the cell for its channel. In this regard, the object reflectors for each channel may be positioned such that their centers are in a plane that includes the field reflector diameter and the field reflector axis.

Relative to the tilt of each object reflector 14, 16, consider the field reflector 12 and object reflectors lying in a coordinate system (x, y, z) with origin at the center of the field reflector, and the z-axis along the optical axis, as shown in FIGS. 1-3. In such an instance, a given object reflector center may be located at (x1, 0, z1), but the object reflector may be tilted at an angle (tilt angle) along an axis (tilt angle axis) parallel to the y-axis and through the point (x1, 0, z1). In other words, consider that as a segment of a parent object reflector, the center of each object reflector may lie on a secondary axis of the parent object reflector. However, the object reflector may be tilted such that, as a characteristic of the object reflector, the secondary axis still goes through the center of the object reflector but is offset from the center of curvature of the parent object reflector.

As also shown in FIGS. 2 and 3, the aperture of each object reflector 14, 16 as a segment of a common parent object reflector may be wedge or leaflet-shaped. In such instances, the object reflectors may be arranged around a point in a quatrefoil (four-leaf clover) shape—the respective point being the center point of their common parent object reflector. Also, the size of the object reflectors may be different for different channels so that energy throughput may be optimized for each channel, particularly when the cell 10 includes three or more channels. In these instances, object reflectors having different sizes may have correspondingly different apex angels. Furthermore, in most instances, the tilt angle of the object reflector pair will be symmetric and carefully selected to control the path desired for the respective channels. Different channels may have different path lengths, if desired.

The field reflector 12 and object reflectors 14, 16 may be mounted at opposite ends of a tube or chamber 18 (shown in FIG. 2, but omitted from FIG. 3 for clarity). In operation in various contexts, the chamber may include a sample medium and/or a base medium (e.g., ambient air) to be analyzed. In such contexts, the sample and base medium can have any of a number of different forms through which the beam of radiation is at least partially transmissive. For example, the sample and base medium can comprise a solid, liquid, gas, plasma or aerosol. More particularly, in various example embodiments, the base medium of ambient air may be in gas form, while a sample may be in gas or aerosol form.

To pass beams of radiation through the dual-channel optical cell 10, the cell may include a transmitter or source 20 and receiver or detector 22 for each channel (shown as source 20a and detector 22a for the first channel, and source 20b and detector 22b for the second channel). Each source may comprise any of a number of different sources configured to transmit a beam of radiation (electromagnetic wave), and each detector may comprise any of a number of different detectors configured to detect or otherwise measure a beam of radiation. For example, one or both of the sources may include a photomixer transmitter that may be directly coupled to the cell, or may be indirectly coupled to the cell via a respective optical path (e.g., optical fiber). Similarly, one or both of the receivers may include an electric-field detector such as a photomixer receiver (homodyne receiver), which may be directly or indirectly coupled to the cell. Microwave and terahertz antennae may also be used as both sources and receivers, and lasers as sources depending on applications.

The sources 20 and detectors 22 may be situated proximate the end of the chamber 18 including the field reflector 12, either inside or outside the area of the field reflector. When a source or detector is situated inside the area of the field reflector, the chamber and/or field reflector may define an opening or port for coupling the respective source or detector to the interior of the chamber, as shown. Alternatively, when a source or detector is situated outside the area of the field reflector, only the chamber itself may define an opening or port for coupling the respective source or detector to the interior of the chamber.

For each channel, the axes of the object reflectors 14, 16 (rotated secondary axes of the parent object reflector through the centers of the object reflectors) may pass through the reflective surface of the field reflector 12, and the optical axis of the field reflector (e.g., coinciding with the optical axis of the parent object reflector) may pass through a common point approximately equidistant between the respective object reflectors. As shown in FIG. 3, for each channel, a beam 24 introduced to the cell 10 via a respective source 20 may be directed to a first one of the object reflectors (e.g., object reflector 14) of the pair of object reflectors of the channel, which reflects the beam back to the field reflector. The field reflector reflects the beam to a second one of the object reflectors (e.g., object reflector 16) of the pair of object reflectors for the channel. The second object reflector reflects the beam back to the field reflector, which reflects the beam back to the first object reflector. The beam then continues to reflect between the field reflector and the object reflectors until the beam reaches the respective detector 22. The distance between the optical axes of the object reflectors, the distance between the field and object reflectors, and the diameter or size of the field reflector (in a direction parallel to a line through the source and detector locations) may affect the number of reflections between the field and object reflectors, and thus the length of the optical path traversed by a beam through the cell 10. More importantly, the angle (tilt angle) of the object reflectors may provide fine tune control of the number of reflections and path length.

Generally, any beam directed from a THz source has a very short Rayleigh length (the distance over which a collimated beam can stay collimated) and, therefore, expands like a spherical wave to the first object reflector (e.g., object reflector 14). The first object reflector refocuses the beam to a spot on the field reflector 12, which starts a line sequence of spots below and near the detector hole in the reflector. The reflected light re-expands the beam to the second object reflector (e.g., object reflector 16) which refocuses the beam to a spot on the field reflector near the position of the source hole and starts a second line of spots in a plane containing the line joining the centers of source and detector centers. And from this corresponding point, the field reflector directs the beam back to the first object reflector. This process continues adding spots on the field reflector until a spot on the source detector line reaches the detector port and collected by the detector.

The channels and their respective object reflectors 14, 16, source 20 and detector 22 may be arranged in any of a number of different manners to carry out the above operation for the respective channel, which may be performed at different times or simultaneously. For each channel, for example, the source 20 and detector 22 may lie along a chord of the field reflector 12 that is displaced from, but parallel to, the diameter of the field reflector; and along this chord, the source and detector may be positioned equidistant from the field reflector axis. The source may be positioned along the line proximate an outer edge of the field reflector. The respective detector may then be positioned along the line relative to the source so as to have sufficient, if not maximum, coupling of any beam introduced into the cell 10 by the source and received by the detector.

Also for each channel, the object reflectors 14, 16 (tilted at respective tilt angles), and the source 20 and detector 22 may be positioned such that the source and detector, and the centers of the object reflectors, lie in the same plane. And when the respective source and detector lie on a chord of the field reflector 12 as indicated above, the plane in which the source and detector, object reflectors lie may be tilted some what from the axis (optical axis) of the field reflector. The tilt angle axis of the object reflectors, then, may be perpendicular to the chord along which the source and detector lie, and perpendicular to the optical axis of the field reflector.

In the example embodiment shown in FIGS. 2 and 3, the source 20a and detector 22a, and the centers of the object reflectors 14a, 16a, lie in a plane slightly inclined to the axis of the field reflector; and the source 20b and detector 22b, and the centers of the object reflectors 14b, 16b, lie in a nearly orthogonal plane slightly inclined to the axis of the field reflector. In an example dual-channel optical cell 10, then, the channels may be arranged in an orthogonal configuration. As shown in FIGS. 1 and 2, a beam in a first channel (shown as beam 24a) may generally propagate in a region orthogonal to the region in which a beam in a second channel (shown as beam 24b) propagates.

The cell design may position of the detector 22 and the source 20 at the above-reference symmetric positions, which may correspond to be beam waist positions. Sources like photomixers, THz horn antennae or the like may have desired positions in their device for the waist location. With this knowledge, the various devices may be mounted in the cell 10 in their appropriate position. When used for a THz spectrometer application, however, the cell may be designed so that the object reflectors 14, 16 image the source waist onto the field reflector 12 with multiple image spots. The design may be optimized by conventional optical design. Terahertz however may impose an additional constraint, the variation of wavefront radius of curvature with path length and wavelength.

As explained in the background section, beam propagation as a function of wavelength may cause severe shifts in focus over a wide band of THz wavelengths. These issues may cause aberrated spots and loss of throughput as the beam divergence may vary significantly with wavelength. In this regard, the beam may be considered astigmatic such that the focus of the beam on the field reflector 12 varies over frequencies in a band of interest (varies over frequencies of interest). This may be seen in FIG. 4, which illustrates an example of the irradiance (power per area) of a beam that may be measured by the detector. Thus, in one example embodiment, the detector may be positioned proximate an outer edge of the field detector at a point that maximizes the irradiance of the beam in the center of the detector at a frequency of interest (e.g., center frequency in a band of interest). The detector may then be sized so as to detect or otherwise measure most if not all of the energy of the beam. In the example of FIG. 4, the beam has a frequency of 500 GHz and the detector has a length and width (or diameter for a circular detector) of 8 mm. In the spectral region of interest, and in particular in the THz spectral region, each channel of the multi-channel optical cell of example embodiments of the present invention may be designed for its own respective band; and in the case of successive bands, the multi-channel optical cell may effectively cover a wider band encompassing the channels' bands.

As an example, different channels of the cell 10 may be optically optimized for different center frequencies using different radii of curvature expected from a source 20 at different wavelengths. This may cause a change of the source position to better match the beam wavefront curvature with the object reflector curvature and/or an adjustment of the source detector position from one channel to another.

As a more particular example of a dual-channel optical cell 22, consider a cell designed for the near infrared. The source 20 may be designed to transmit a beam with a radius of curvature equal to the source-object reflector distance because the radii of curvature (ROC's) of the reflectors (field and object reflectors 12, 14, 16) may have this same ROC, for example 200 mm. Now, consider this cell used at THz frequencies for channels having bandwidths of approximately 200 GHz centered at 400 GHz and 200 GHz centered at 600 GHz. In this example, the field reflector 12 has a radius of curvature of approximately 200 mm, and the object reflectors 14, 16 have ROC's of approximately 200 mm and are located 200 mm from the field reflector. With these values, a THz source with a 4 mm waist produces a ROC of 222.46 mm at 400 GHz, and 250.53 mm at 600 GHz, and the ROC varies over each band unlike the behavior in the infrared. One solution may be to adjust the position of the first channel source so it matches the ROC of the object reflector, and likewise for the second source, but this may lead to unacceptable source placements. A better solution would be to redesign the cell and replace the 200 mm elements with an optimized match to the 400 and 600 GHz band centers. It should be noted that optimization may select the best distance between the field reflector and object reflectors and the ROC's of the reflectors as a response to the changes in the ROC of the source beam over both bands. This design optimization is unique to terahertz applications of the multipath cell and is irrelevant for visible and infrared applications because the source ROC may be approximately constant in these applications.

In addition to improving ROC performance by having two THz channels over one channel, the cell design may allow the designer to use different sources for the two channels. In such instances, the sources for the two channels may have different source beam waists, which may add an additional degree of freedom to the optimization process. This process may contribute to the overall improved instrument spectrometer sensitivity.

As indicated above, although the multi-channel optical cell of one example embodiment is a dual-channel optical cell, the multi-channel optical cell may include three, four or more channels depending upon operating wavelength and path length requirements. An example of a three-channel optical cell 26 is shown in FIG. 5, without an accompanying tube or chamber which has been omitted for clarity. As shown, similar to the dual-channel optical cell, the three-channel optical cell may include a concave field reflector 28 and a pair of object reflectors 30, 32 for each channel (shown as object reflectors 30a, 32a for a first channel, 30b, 32b for a second channel, and 30c, 32c for a third channel). Similar to the object reflectors of the dual-channel optical cell, the object reflectors of the three-channel design may be separate reflectors, or two or more of the object reflectors may be formed from a single reflector.

The field reflector 28 and object reflectors 30, 32 may be concave reflectors that have reflecting surfaces of any of a number of different shapes. In one example embodiment, the reflectors including the field and object reflectors, are spherical, concave reflectors that have approximately the same radius of curvature. As shown in FIG. 5, for example, the object reflectors may be arranged in a circle around a point on the optical axis of the field reflector that is equidistant between the object reflectors. One may desire different path lengths for different channels. In this case, the tilt angles of the object reflector pairs for different channels may be different to thereby allow a different number of spots on the field reflector and subsequent different path lengths. This may be useful if one channel is used to measure strongly absorbing spectral lines that might be in saturation. Using a shorter path length for this channel may provide a non-saturated measurement.

Also similar to the two-channel optical cell 10, the three-channel optical cell 26 may include a transmitter or source 34 and receiver or detector 36 for each channel (shown as source 34a and detector 36a for the first channel, and sources 34b and 34c for the second and third channels, respectively—the detectors for the second and third channels being hidden behind the beams in FIG. 5). The components of each channel, including the channel's object reflectors 30, 32, and source and detector, may be situated and arranged in any of a number of different manners to carry out an operation for the respective channel in a manner similar to that described above. For example, the source and detector may lie along a chord of the field reflector that is displaced from, but parallel to, the diameter of the field reflector, and may be positioned relative to one another in a manner that may vary as a function of the waist of the beam and its divergence.

In the dual-channel optical cell 10, the components may be arranged such that the source 34 and detector 36, and the centers of the object reflectors 30, 32, of one channel lie in a distinct plane, which may be inclined to the axis of the field reflector 12. In the three-channel design, and for the multi-channel optical cell in general, these planes may be arranged so as to intersect with a non-obtuse (acute or right) angle of intersection approximately equal to 360°/2n, where n represents the number of channels (e.g., 3). In other words, the planes may be arranged so as to intersect about a common point (e.g., axis of parent object reflector, which may coincide with the optical axis of the field reflector), and be rotated from one another about the z-axis at an angle approximately equal to 360°/2n. Thus, for the dual-channel design, the planes may be arranged so as to intersect with a right angle of intersection of approximately 90° (i.e., 360°/4); and for the three-channel design, the planes may be arranged so as to intersect with an acute angle of intersection of approximately 60° (i.e., 360°/6).

The multi-channel cell of example embodiments of the present invention may be implemented in any of a number of contexts, including different types of spectrometer systems. One such spectrometer system and method that may benefit from exemplary embodiments of the present invention is described in U.S. patent application Ser. No. 12/712,736, entitled: System and Method for Magnitude and Phase Retrieval by Path Modulation, filed Feb. 25, 2010. The content of the '736 application is hereby incorporated by reference in its entirety.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An apparatus comprising:
a field reflector having an optical axis and a reflective surface;
a plurality of pairs of object reflectors each of which has a reflective surface arranged to face the reflective surface of the field reflector; and
a plurality of source port and detector port pairs facing the reflective surfaces of the object reflectors, the source port and detector port of each pair being positioned proximate an outer edge of the field reflector such that the optical axis of the field reflector lies between the respective source port and detector port, wherein each source port is configured to pass a beam of radiation to propagation between the field reflector and object reflectors, and each detector port is configured to receive a beam of radiation propagating between the field reflector and object reflectors,
wherein the object reflectors and source port and detector port pairs are arranged such that each source port and detector port pair is associated with a respective pair of object reflectors forming a distinct channel, and wherein the source port and detector port pair, and centers of the associated pair of object reflectors, of each channel lie in a distinct plane.

2. The apparatus of claim 1, wherein the object reflectors and source port and detector port pairs are arranged such that the distinct planes of the channels intersect with a non-obtuse angle of intersection of approximately 360°/2n, where n represents the number of channels.

3. The apparatus of claim 1, wherein the object reflectors are arranged around a common point on the optical axis of the field reflector.

4. The apparatus of claim 3, wherein for each channel, the source port and detector port lie on a chord of the field reflector, and the object reflectors are tilted at an angle along an axis perpendicular to the respective chord and perpendicular to the optical axis of the field reflector.

5. The apparatus of claim 4, wherein for each channel, the chord along which the source port and detector port lie is displaced from the diameter of the field reflector.

6. The apparatus of claim 3, wherein the field and object reflectors comprise spherical, concave reflectors, arranged in a quatrefoil shape or a circle around the common point.

7. The apparatus of claim 3, wherein the common point is equidistant between the object reflectors.

8. The apparatus of claim 1, wherein for each channel, the field reflector, source port and detector port pair, and associated pair of object reflectors are arranged such that a beam of radiation passed by the source port propagates and reflects between the field reflector and respective pair of object reflectors until the beam reaches the respective detector port.

9. The apparatus of claim 1, wherein each source port is configured to pass a beam of radiation in a distinct frequency band.

10. The apparatus of claim 9, wherein each source port is configured to pass a beam of radiation in a distinct frequency band in the terahertz spectral region.

11. The apparatus of claim 9, wherein the plurality of source port and detector port pairs include at least a first source port and a second source port, the first source port being configured to pass a beam of radiation in the terahertz spectral region, and the second source port being configured to pass a beam of radiation in the infrared or visible spectral region.

12. The apparatus of claim 9, wherein the plurality of source port and detector port pairs include at least a first source port, a second source port and a third source port, the first source port being configured to pass a beam of radiation in the terahertz spectral region, the second source port being configured to pass a beam of radiation in the infrared spectral region, and the third source port being configured to pass a beam of radiation in the visible spectral region.

13. An apparatus comprising:
a field reflector having an optical axis and a reflective surface;
a first channel comprising:
  a first pair of object reflectors each of which has a reflective surface arranged to face the reflective surface of the field reflector; and
  a first source port and a first detector port positioned proximate an outer edge of the field reflector such that the optical axis of the field reflector lies between the first source port and first detector port, wherein the first source port and first detector port, and centers of the first pair of object reflectors, lie in a first plane; and
a second channel comprising:
  a second pair of object reflectors each of which has a reflective surface arranged to face the reflective surface of the field reflector; and
  a second source port and a second detector port positioned proximate the outer edge of the field reflector such that the optical axis of the field reflector lies between the second source port and second detector port, wherein the second source port and second detector port, and centers of the second pair of object reflectors, lie in a second plane that is distinct from the first plane.

14. The apparatus of claim 13, wherein the first and second pairs of object reflectors and the first and second source ports and detector ports are arranged such that the first and second planes intersect at approximately a right angle.

15. The apparatus of claim 13, wherein the first and second pairs of object reflectors are arranged around a common point on the optical axis of the field reflector.

16. The apparatus of claim 15, wherein the first source port and first detector port lie on a first chord of the field reflector, and the object reflectors of the first pair of object reflectors are tilted at an angle along an axis perpendicular to the first chord and perpendicular to the optical axis of the field reflector, and
wherein the second source port and second detector port lie on a second chord of the field reflector, and the object reflectors of the second pair of object reflectors are tilted at an angle along an axis perpendicular to the second chord and perpendicular to the optical axis of the field reflector.

17. The apparatus of claim 16, wherein each of the first chord along which the first source port and first detector port lie, and the second chord along which the second source port and second detector port lie, is displaced from the diameter of the field reflector.

18. The apparatus of claim 15, wherein the field and object reflectors comprise spherical, concave reflectors, arranged in a quatrefoil shape or a circle around the common point.

19. The apparatus of claim 15, wherein the common point is equidistant between the object reflectors.

20. The apparatus of claim 13, wherein the field reflector, first pair of object reflectors, and first source port and first detector port are arranged such that a first beam of radiation passed by the first source port propagates and reflects between the field reflector and respective first pair of object reflectors until the first beam reaches the first detector port, and
wherein the field reflector, second pair of object reflectors, and second source port and second detector port are arranged such that a second beam of radiation passed by the second source port propagates and reflects between the field reflector and respective second pair of object reflectors until the second beam reaches the second detector port.

21. The apparatus of claim 13, wherein the first and second source ports are configured to pass beams of radiation in respective, distinct frequency bands.

22. The apparatus of claim 21, wherein the first and second source ports are configured to pass beams of radiation in respective, distinct frequency bands in the terahertz spectral region.

23. The apparatus of claim 21, wherein the first source port is configured to pass a beam of radiation in the terahertz spectral region, and the second source port is configured to pass a beam of radiation in the infrared or visible spectral region.

24. The apparatus of claim 13 further comprising a third channel, the third channel comprising:
a third pair of object reflectors each of which has a reflective surface arranged to face the reflective surface of the field reflector; and
a third source port and a third detector port positioned proximate the outer edge of the field reflector such that the optical axis of the field reflector lies between the third source port and third detector port, wherein the third source port and third detector port, and centers of the third pair of object reflectors, lie in a third plane that is distinct from the first and second planes.

25. The apparatus of claim 24, wherein the first, second and third pairs of object reflectors and the first, second and third source ports and detector ports are arranged such that the first, second and third planes intersect at approximately a 60° angle.

26. The apparatus of claim 24, wherein the first source port is configured to pass a beam of radiation in the terahertz spectral region, the second source port is configured to pass a beam of radiation in the infrared spectral region, and the third source port is configured to pass a beam of radiation in the visible spectral region.

27. An apparatus comprising:
a field reflector having an optical axis and a reflective surface;
a plurality of pairs of object reflectors each of which has a reflective surface arranged to face the reflective surface of the field reflector; and
a plurality of source port and detector port pairs facing the reflective surfaces of the object reflectors, the source port and detector port of each pair being positioned proximate an outer edge of the field reflector such that the optical axis of the field reflector lies between the respective source port and detector port,
wherein the object reflectors and source port and detector port pairs are arranged such that each source port and detector port pair is associated with a respective pair of object reflectors forming a distinct channel, the pair of object reflectors of different channels have different optical properties for supporting different frequency bands,
wherein for each channel, the source port and detector port pair, and centers of the associated pair of object reflectors, lie in a distinct plane, and
wherein for each channel, the source port is configured to pass a beam of radiation in a distinct frequency band to propagation between the field reflector and the associated pair of object reflectors, and the detector port is configured to receive a beam of radiation propagating between the field reflector and associated pair of object reflectors.

* * * * *